United States Patent [19]

Gasson et al.

[11] 3,960,925

[45] June 1, 1976

[54] PRODUCTION OF ACRYLONITRILE BY AMMOXIDATION OF PROPYLENE

[75] Inventors: Edward James Gasson, Dollar; Thomas Charles Krosnar, Polmont; Stanley Frederic Marrian, Aberdour, all of Scotland

[73] Assignee: BP Chemicals International Limited, London, England

[22] Filed: Aug. 22, 1974

[21] Appl. No.: 499,440

[30] Foreign Application Priority Data

Sept. 7, 1973 United Kingdom............... 42130/73

[52] U.S. Cl. ........................................... 260/465.3
[51] Int. Cl.² ...................................... C07C 120/14
[58] Field of Search ................................ 260/465.3

[56] References Cited

UNITED STATES PATENTS

| | | | |
|---|---|---|---|
| 2,904,580 | 9/1959 | Idol, Jr. .............................. | 260/465.3 |
| 3,431,292 | 3/1969 | Callahan et al. ................... | 260/465.3 |
| 3,849,337 | 11/1974 | Manara et al. ................ | 260/465.3 X |

FOREIGN PATENTS OR APPLICATIONS

| | | | |
|---|---|---|---|
| 1,007,929 | 10/1965 | United Kingdom.............. | 260/465.3 |
| 1,176,233 | 1/1970 | United Kingdom.............. | 260/465.3 |

*Primary Examiner*—Joseph P. Brust
*Attorney, Agent, or Firm*—Brooks Haidt Haffner & Delahunty

[57] ABSTRACT

Production of acrylonitrile by ammoxidation of propylene using as catalyst an oxide composition containing antimony, uranium and titanium together with copper, iron and/or vanadium.

14 Claims, No Drawings

PRODUCTION OF ACRYLONITRILE BY AMMOXIDATION OF PROPYLENE

The present invention relates to the production of unsaturated aliphatic nitriles and in particular to the production of acrylonitrile.

It is known from British patent specification No. 971,038 (The Standard Oil Company) to produce unsaturated nitriles from olefins by contacting in the vapour phase at an elevated temperature at which nitrile formation proceeds, a mixture of an olefin having only 3 carbon atoms in a straight chain, ammonia and oxygen, said mixture of ammonia, olefin and oxygen having a molar ratio of ammonia to olefin of from 0.51:1 to 5:1 and a molar ratio of oxygen to olefin of from 0.5:1 to 4:1 with a catalyst composition consisting essentially of oxides of antimony and uranium as essential catalytic ingredients, the Sb:U atomic ratio being within the range of from 1:50 to 99:1. It is also known from British patent specification No. 1,007,929 (The Distillers Company Limited) to produce acrylonitrile by reacting at an elevated temperature in the vapour phase, propylene, molecular oxygen and ammonia over an oxide composition comprising antimony, uranium, oxygen and a polyvalent metal of atomic number 22 to 41, 44 to 49, 73, 77 to 83 or 90 as catalyst. A particular composition contains antimony and uranium, together with copper, iron or titanium. The atom ratio of the metal atoms of the composition are disclosed as antimony to uranium from about 1:1 to 20;1 preferably 2:1 to 10:1 and the ratio of uranium to the polyvalent metal from about 1:1 to 10:1.

The oxide compositions disclosed as catalysts in these prior British patent specifications have certain disadvantages when used commercially. Thus with the composition disclosed in British patent specification No. 971,038 it is necessary to employ a large stoichiometric excess of ammonia e.g. up to 50% excess in order to obtain a satisfactory yield of nitrile based on the olefin fed and also large amounts of by product acrolein and/or acetonitrile are produced. According to British patent specification No. 1,007,929 this disadvantage is largely overcome by the presence of other metal components such as copper, iron or titanium in the oxide composition catalyst. However, there remains the disadvantage that a relatively large proportion of uranium is required in these catalysts to obtain the highest acrylonitrile yields; for example, in British patent specification No. 971,038 uranium contents of the catalyst of 12–14 atom % were needed. Uranium is a toxic and slightly radioactive element which, therefore, presents handling and disposal problems. It is, therefore, desirable from a commercial viewpoint to keep the uranium concentration in these catalyst compositions as low as possible and consistent with obtaining a satisfactorily high yield of nitrile from the process.

It has now been found that by use of such catalyst compositions which also contain titanium in amount in excess of that previously disclosed it is possible to reduce the amount of uranium to a relatively low level without reducing the yield of acrylonitrile produced.

Accordingly the present invention is a process for the production of acrylonitrile which comprises reacting at an elevated temperature in the vapour phase propylene, molecular oxygen and ammonia over an oxide composition containing antimony, uranium and titanium together with copper, iron and/or vanadium wherein the atomic ratio of antimony to titanium is in the range 1:1 to 12:1, antimony to copper, iron and/or vanadium in the range 2:1 to 15:1 and wherein the uranium content of the composition is in the range 1 to 10 atom % of the total metal content of the composition.

The oxide composition catalysts of the present invention may be regarded either as mixtures of oxides of the various metals or as oxygencontaining compounds of the metals; under the reaction conditions either or both forms may be present.

The catalysts may be prepared, for instance, by intimately mixing the oxides or compounds yielding the oxides on heating, or by coprecipitation of the oxides, hydrated oxides or insoluble salts, from aqueous solution. The copper, iron and/or vanadium oxide or compound may be added during or after the admixture of the antimony, uranium and titanium oxides or compounds. Compounds of antimony, uranium and titanium which may be used in the manufacture of the catalysts include antimony trioxide, antimony tetroxide, antimony pentoxide or mixtures of such oxides; uranium dioxide, titanium dioxide, uranium trioxide, uranoso-uranic oxide ($U_3O_8$), uranyl salts such as uranyl acetate, ammonium uranate, titanium salts such as titanium tetrachloride, titanium alkoxides or mixtures of such compound. Hydrated forms of the oxides may also be used, for instance, compounds such as are formed by the action of aqueous nitric acid on antimony metal or uranium metal. Particularly suitable compounds of polyvalent metals are nitrates or chlorides.

It is preferred to give the catalyst a prior heat-treatment for instance at a temperature between 700° and 1000°C in a molecular oxygencontaining gas.

The reaction of propylene with oxygen and ammonia over the catalysts may be carried out in any suitable manner, for instance as a fixed bed process in which the catalyst is used in the form of granules or pellets, or as a fluidised bed process, or as a moving bed process.

The proportion of propylene in the feed to the reaction may vary within fairly wide limits, for example, between 1 and 20% by volume of the feed, and suitably between 2 and 10% volume. It is preferred to use between 6 and 8% volume of propylene in the feed.

The concentration of oxygen in the feed may also vary within moderately wide limits, for example, between 1 and 20% by volume. The oxygen may be diluted with inert gases, and may be for example, supplied as air.

The reaction is suitably carried out in the presence, as diluent, of a gas which is substantially inert under the conditions of reaction, for example, nitrogen, propane, butane, isobutane, carbon dioxide or steam. It is preferred to carry out the reaction in the presence of steam or mixtures of steam and nitrogen. The concentration of the steam may vary within wide limits, for instance between zero and 60% by volume of the feed.

The concentration of ammonia may also vary within moderately wide limits, for instance, between 2 and 10% by volume of the feed. If the maximum yield of acrylonitrile on propylene is required, it is desirable to use an excess of ammonia over propylene. The preferred concentration of ammonia is between 1 and 1.1 times the concentration of propylene.

The reaction is carried out at an elevated temperature, preferably between 300° and 550°C.

The contact time, defined as the volume of catalyst divided by the flow of gas per second calculated at room temperature and pressure, may be, for example in the range 1 – 30 seconds.

and 19.5% steam (by volume). Test results are shown in the table.

TABLE

| Example | Catalyst Composition | | | | | Heat treatment temperature °C | Reaction temperature °C | Yields (Molar) on propylene fed (%) | | recovered C₃H₆ | AN Efficiency % |
|---|---|---|---|---|---|---|---|---|---|---|---|
| | Sb | Ti | U | | | | | AN | CO₂ | | |
| 1 | 3 | 1 | 0.25 | 0.25 Cu | — | 780 | 479 | 75.8 | 9.0 | 3.5 | 78.5 |
| 2 | 3 | 1 | 0.25 | 0.5 Cu | — | 780 | 489 | 73.5 | 13.2 | 1.1 | 74.3 |
| 3 | 3 | 1 | 0.5 | 0.5 Cu | — | 830 | 480 | 75.0 | 12.3 | 0.2 | 75.2 |
| 4 | 3 | 0.5 | 0.25 | 0.25 Cu | — | 780 | 507 | 71.3 | 11.7 | 3.1 | 73.6 |
| 5 | 3 | 1 | 0.25 | 0.25 Fe | — | 780 | 488 | 68.3 | 11.3 | 7.3 | 73.7 |
| 6 | 3 | 1 | 0.25 | 0.25 Cu | 0.125V | 810 | 471 | 65.3 | 12.4 | 3.1 | 67.4 |
| 7 | 3 | 1 | 0.25 | 0.25 Cu | 1.0 Fe | 830 | 460 | 71.1 | 11.0 | 5.5 | 75.2 |

The reaction may be carried out at atmospheric pressure, or at super- or sub-atmospheric pressures. It is preferred to operate at a pressure of 1 – 5 atmospheres absolute.

The acrylonitrile may be recovered from the reaction products in any suitable manner, for example by extraction with water, preferably at acid pH, followed by fractional distillation. In one method the hot reaction gases are contacted firstly with a cold dilute aqueous solution of sulphuric acid which neutralises excess ammonia and extracts some of the nitrile, and secondly with cold water to extract the remainder of the nitrile; the nitrile is subsequently recovered from the extractions by fractional distillation.

The process of the present invention is illustrated further with reference to the following examples, in which, unless otherwise specified, all parts are to be weight.

EXAMPLE 1

A catalyst of atomic composition Sb/Ti/U/Cu = 3/1/0.25/0.25 was prepared as follows: n Butyltitanate (340.4 parts) was added drop-wise to a stirred mixture of water (800 parts) and nitric acid (227 parts). Antimony trioxide (438 parts) was suspended in the mixture and $UO_2(NO_3)_2 \cdot 6H_2O$ (125.4 parts) in water (200 parts) and $CU(NO_3)_2 \cdot 3 H_2O$ (60.6 parts) in water (200 parts) were added. The temperature was raised to 40°C and the stirred mixture was neutralised with aqueous ammonia (10%) to pH 6.4. The mixture was allowed to cool and was filtered. The cake was re-suspended in water (7000 parts), stirred for 30 minutes and filtered. The cake was dried at 120°C, sieved and pelleted to cylinders of 4 mm diameter and 4 mm length. The pellets were heat treated in a furnace in which the temperature was raised at 22°C per hour and in which an air stream was injected at a rate of 50 liters/h/kg catalyst. When the temperature reached 780°C, it was maintained for 16 hours before the charge was cooled. The results obtained on testing the catalyst in a glass reactor with a feed of 5% propylene, 6% ammonia, 60% air and 29% steam (by volume) are shown in the table.

EXAMPLES 2 – 7

The catalysts used in examples 2 – 7 were prepared in the same way as the catalyst in example 1, the proportions of reagents being altered to provide differing compositions. For catalysts containing iron, the appropriate quantity of ferric nitrate was added with the other water soluble components. Vanadium was added as the sieved pentoxide by stirring in during the final wash of the catalyst cake.

The catalysts were tested in the same way as that in example 1 except for example 7 where the ratio of the feed gases was 6% propylene, 6.5% ammonia, 68% air,

We claim:

1. A process for the production of acrylonitrile which comprises reacting at an elevated temperature in the vapor phase propylene, molecular oxygen, and ammonia over an oxide composition containing as the sole catalytic materials a mixture of oxides of the metals or oxygen containing compounds of the metals antimony, uranium, titanium and a metal selected from the group consisting of copper, iron, vanadium and mixtures thereof wherein the atomic ratio of antimony to each of copper, iron and vanadium is in the range 2:1 to 15:1, and wherein the uranium content of the composition is in the range of 1 to 10% of the total metal content of the composition.

2. A process as claimed in claim 1 wherein the oxide composition is heated before use to a temperature between 700° and 1000°C in a molecular oxygencontaining gas.

3. A process as claimed in claim 1 wherein the proportion of propylene in the reactant feed is between 2 and 10% by volume.

4. A process as claimed in claim 1 wherein the concentration of oxygen in the reactant feed is between 1 and 20% by volume.

5. A process as claimed in claim 1 wherein the reaction is carried out in the presence of a gaseous diluent selected from nitrogen, propane, butane, isobutane, carbon dioxide and steam.

6. A process as claimed in claim 5 wherein the diluent is steam in concentration of up to 60% by volume of the reactant feed.

7. A process as claimed in claim 1 wherein the concentration of ammonia in the reactant feed is between 1 and 1:1 times the concentration of propylene in the feed.

8. A process as claimed in claim 1 wherein the reaction is carried out at an elevated temperature between 300° and 550°C.

9. A process as claimed in claim 1 wherein the contact time, as herein before defined, is in the range of 1 to 30 seconds.

10. A process as claimed in claim 1, wherein the oxide composition is prepared from an admixture of the oxides of said metals.

11. A process as claimed in claim 1, wherein the oxide composition is prepared from an admixture of compounds yielding the oxides of said metals on heating.

12. A process as claimed in claim 1, wherein the oxide composition is prepared by co-precipitation of the oxides of metals. said 13. A process as claimed in claim 1, wherein the oxide composition is prepared by co-precipitation of the hydrated oxides of said metals.

14. A process as claimed in claim 1, wherein the oxide composition is prepared by co-precipitation of insoluble salts from aqueous solution.

\* \* \* \* \*

UNITED STATES PATENT OFFICE
CERTIFICATE OF CORRECTION

PATENT NO. : 3,960,925

DATED : June 1, 1976

INVENTOR(S) : EDWARD JAMES GASSON, THOMAS CHARLES KROSNAR and STANLEY FREDERIC MARRIAN It is certified that error appears in the above—identified patent and that said Letters Patent are hereby corrected as shown below:

Column 4, line 63, insert --said-- after "of" and before "metals" and delete the word "said" after the period (.).

Signed and Sealed this

Twenty-first Day of December 1976

[SEAL]

Attest:

RUTH C. MASON
*Attesting Officer*

C. MARSHALL DANN
*Commissioner of Patents and Trademarks*